(12) United States Patent
Walter et al.

(10) Patent No.: US 7,263,167 B2
(45) Date of Patent: Aug. 28, 2007

(54) DIRECT CONVERSION X-RAY DETECTOR WITH OVER-RANGE AND PILE-UP CORRECTION

(75) Inventors: Deborah Joy Walter, Burnt Hills, NY (US); John Eric Tkaczyk, Delanson, NY (US); Yanfeng Du, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/239,962

(22) Filed: Sep. 30, 2005

(65) Prior Publication Data

US 2007/0076848 A1    Apr. 5, 2007

(51) Int. Cl.
*H05G 1/26* (2006.01)
(52) U.S. Cl. .......................................... 378/116; 378/19
(58) Field of Classification Search .............. 378/4–20, 378/62, 98.8, 97, 196–198, 108, 116, 207; 250/370.09
See application file for complete search history.

(56) References Cited

U.S. PATENT DOCUMENTS

| | | | |
|---|---|---|---|
| 5,225,682 A | 7/1993 | Britton, Jr. et al. | 250/395 |
| 5,789,737 A * | 8/1998 | Street | 250/208.1 |
| 6,403,960 B1 | 6/2002 | Wellnitz et al. | 250/363.09 |
| 6,764,217 B2 * | 7/2004 | Yasuda et al. | 378/205 |
| 2004/0174959 A1 * | 9/2004 | Green | 378/146 |

FOREIGN PATENT DOCUMENTS

EP    0705446    11/1998

* cited by examiner

*Primary Examiner*—Hoon Song
(74) *Attorney, Agent, or Firm*—Fletcher Yoder

(57) ABSTRACT

A method of scanning a subject to be imaged is presented. The method includes acquiring projection data from a first region of a pixel, where the first region has a first area. Additionally, the method includes acquiring projection data from a second region of the pixel, where the second region has a second area. The method also includes combining projection data from the first and second regions to obtain composite projection data for the pixel. Computer-readable medium and systems that afford functionality of the type defined by this method are also contemplated in conjunction with the present technique.

23 Claims, 5 Drawing Sheets

DIRECT CONVERSION X-RAY DETECTOR WITH OVER-RANGE AND PILE-UP CORRECTION

BACKGROUND

The invention relates generally to radiographic detectors for diagnostic imaging, and more particularly to enhancing the flux rate in direct conversion detectors for high flux rate imaging with photon counting and energy discrimination, such as in computed tomography (CT) applications.

Radiographic imaging systems, such as X-ray and computed tomography (CT) have been employed for observing, in real time, interior aspects of an object. Typically, the imaging systems include an X-ray source that is configured to emit X-rays toward an object of interest, such as a patient or a piece of luggage. A detecting device, such as an array of radiation detectors, is positioned on the other side of the object and is configured to detect the X-rays transmitted through the object.

Conventional CT and other radiographic imaging systems utilize detectors that convert radiographic energy into current signals that are integrated over a time period, then measured and ultimately digitized. A drawback of such detectors however is their inability to provide data or feedback as to the number and/or energy of photons detected. Also, energy discriminating, direct conversion detectors capable of not only X-ray counting, but also providing a measurement of the energy level of each X-ray detected have been employed in CT systems. However, a drawback of these direct conversion semiconductor detectors is their inability to count at the X-ray photon flux rates typically encountered with conventional CT systems. Further, the very high X-ray photon flux rate has been known to cause pile-up and polarization that ultimately leads to detector saturation. "Pile-up" is a phenomenon that occurs when a source flux at the detector is so bright that there is a non-negligible possibility that two or more X-ray photons deposit charge packets in a single pixel ("photon pile-up"), or in neighboring pixels ("pattern pile-up"), during one read-out cycle (i.e., one frame). In such a case these events are recognized as one single event having the sum of their energies. If this happens sufficiently often, this will result in a hardening of the spectrum as piled-up soft events are shifted in the spectrum to higher energies. In addition, pile-up leads to a more or less pronounced depression of counts in a central part of a bright source, resulting in flux loss. Pile-up also affects light curves, suppressing high count rates. In other words, these detectors typically saturate at relatively low X-ray flux level thresholds. Above these thresholds, the detector response is not predictable or has degraded dose utilization. That is, once a pixel is saturated (corresponding to a bright spot in the generated signal), additional radiation will not produce useful detail in the image.

Further, as will be appreciated, detector saturation leads to loss of imaging information and consequently results in noise and artifacts in X-ray projection and CT images. Photon counting direct conversion detectors are known to suffer from decreased detector quantum efficiency (DQE) at high count rates mainly due to detector pile-up. In particular, photon counting direct conversion detectors, show pile up due to the intrinsic charge collection time (i.e., dead time) associated with each X-ray photon event. As indicated above, saturation ultimately is often due to pulse pile-up, particularly when the X-ray photon absorption rate for each pixel is on the order of the inverse of this charge collection time. The reciprocal of the charge collection time is called a maximum periodic rate (MPR). When the true mean X-ray count rate incident on the detector is equal to the maximum periodic rate, the DQE is one half and the output count rate recorded is only one half the maximum periodic rate. Reduced DQE results in reduced image quality, i.e., a noisy image. In addition, hysteresis and other non-linear effects occur at flux levels near detector saturation as well as flux levels over detector saturation and lead to image artifacts.

In addition, the relationship between the true signal and the measured signal becomes non-linear, dropping off as the count rate is increased. This pile-up effect, if stable, may then be calibrated and corrected, thereby increasing the effective count rate capability of the detector, albeit with a penalty of higher noise. However, if the count rate is increased to a point where the relationship between the true signal and the measured signal becomes non-monotonic, correction of this non-monotonic relationship may no longer be practical. In this case the detector is over-ranged, and the count rate at this point becomes the maximum achievable count rate.

Previously conceived solutions to enable photon counting at high X-ray flux rates include using bowtie shaped filters to pre-condition the flux rate at the detector, compensating for the patient shape. Also it has been proposed to subdivide the pixel into multiple sub-pixels, each sub-pixel connected to its own preamplifier. By reducing the area of the direct conversion sub-pixel the flux rate capability may be increased as fewer photons are collected in the smaller area. However, the signal-to-noise ratio of the resulting signal may be reduced, and the level of cross-talk will be disadvantageously significant due to the increased perimeter between sub-pixels.

There is therefore a need for an energy discriminating detector that does not saturate at the X-ray photon flux rates typically found in conventional radiographic systems. In particular, there is a significant need for a design that advantageously combines information from a direct conversion photon counting detector in an optimal way, taking into account associated noise in order to extend the flux rate capability. It would be desirable to improve the flux rate in direct conversion detectors that will allow photon counting in medical and industrial applications that are heretofore unmanageable because either the flux rate or the dynamic range requirements are too high. Additionally, there is a particular need for correction algorithms for known deleterious effects, such as pile-up and pixel over-range.

BRIEF DESCRIPTION

In accordance with aspects of the present technique, a method of scanning a subject to be imaged is presented. The method includes acquiring projection data from a first region of a pixel, where the first region has a first area. Additionally, the method includes acquiring projection data from a second region of the pixel, where the second region has a second area. The method also includes combining projection data from the first and second regions to obtain composite projection data for the pixel. Computer-readable medium and systems that afford functionality of the type defined by this method are also contemplated in conjunction with the present technique.

In accordance with another aspect of the present technique, a radiographic imaging system is presented. The system includes a detector assembly configured to detect a stream of radiation emitted by a radiation source toward a subject to be scanned and to generate one or more signals responsive to the stream of radiation, where the detector assembly includes one or more pixels configured to absorb radiation, where each of the one or more pixels includes a first region having a first area and a second region having a second area; and where the first area is different from the second area.

In accordance with further aspects of the present technique, a radiographic imaging system is presented. The system includes a radiation source configured to emit a stream of radiation toward a subject to be scanned. Further, the system includes a detector assembly configured to detect the stream of radiation and to generate one or more signals responsive to the stream of radiation, where the detector assembly includes one or more pixels configured to absorb radiation, and where each of the one or more pixels includes a first region having a first area and a second region having a second area. The system also includes a system controller configured to rotate the radiation source and the detector assembly and to acquire one or more sets of projection data from the one or more detectors via a data acquisition system. Additionally, the system includes a computer system operationally coupled to the radiation source and the detector assembly, where the computer system is configured to receive the one or more sets of projection data.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
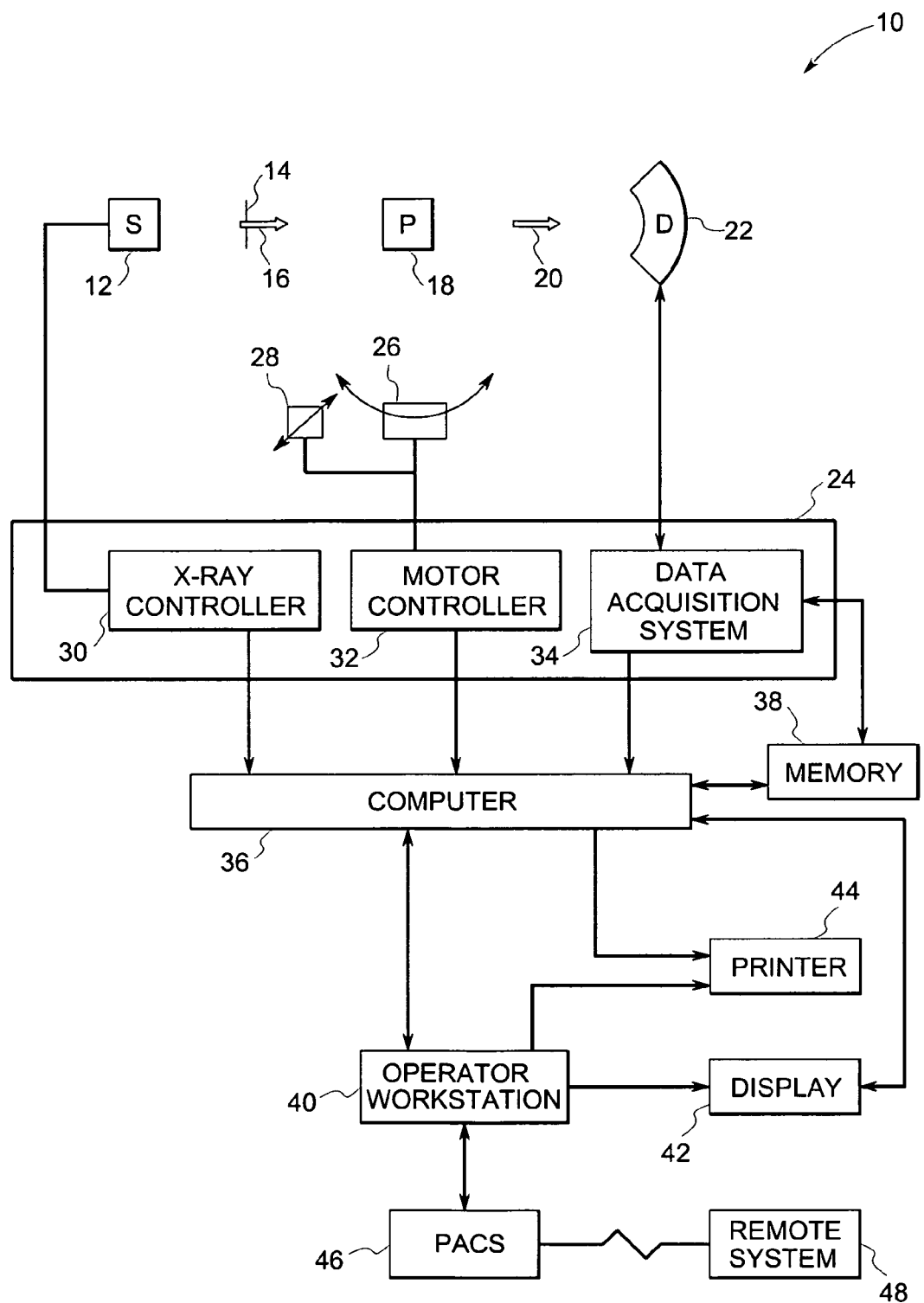
FIG. 1 is a block diagram of an exemplary imaging system in the form of a CT imaging system for use in producing processed images.

FIG. 1 is a block diagram showing an imaging system 10 for acquiring and processing projection data in accordance with the present technique. In the illustrated embodiment, the system 10 is a computed tomography (CT) system designed to acquire X-ray projection data, to reconstruct the projection data into an image, and to process the image data for display and analysis in accordance with the present technique. It should be noted, moreover, that aspects of the present technique may find application outside the field of CT imaging. For example, the invention may also be applied in conventional digital X-ray imaging, X-ray tomosynthesis, digital X-ray mammography, and any other digital radiographic imaging setting. Similarly, while the particular application of the techniques to medical imaging is described below, other technical fields may make use of the invention, such as for part inspection, baggage and parcel inspection, and so forth.

In the embodiment illustrated in FIG. 1, the imaging system 10 includes a source of X-ray radiation 12, such as an X-ray tube. The source of X-ray radiation 12 may include thermionic or solid-state electron emitters directed at an anode to generate X-rays or, indeed, any other emitter capable of generating X-rays having a spectrum and energy useful for imaging a desired object. Examples of suitable electron emitters include tungsten filament, tungsten plate, field emitter, thermal field emitter, dispenser cathode, thermionic cathode, photo-emitter, and ferroelectric cathode.

The source of radiation 12 may be positioned near a collimator 14, which may be configured to shape a stream of radiation 16 that is emitted by the source of radiation 12. The stream of radiation 16 passes into the imaging volume containing the subject to be imaged, such as a human patient 18. The stream of radiation 16 may be generally fan-shaped or cone-shaped, depending on the configuration of the detector array, discussed below, as well as the desired method of data acquisition. A portion 20 of radiation passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

The radiation source 12 is controlled by a system controller 24, which furnishes both power, and control signals for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital projection data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and projection data, interface circuits, and so forth.

In the embodiment illustrated in FIG. 1, the system controller 24 is coupled via a motor controller 32 to a rotational subsystem 26 and a linear positioning subsystem 28. In one embodiment, the rotational subsystem 26 enables the X-ray source 12, the collimator 14 and the detector 22 to be rotated one or multiple turns around the patient 18. In other embodiments, the rotational subsystem 26 may rotate only one of the source 12 or the detector 22 or may differentially activate various stationary electron emitters to generate X-ray radiation and/or detector elements arranged in a ring about the imaging volume. In embodiments in which the source 12 and/or detector 22 are rotated, the rotational subsystem 26 may include a gantry. Thus, the system controller 24 may be utilized to operate the gantry. The linear positioning subsystem 28 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation 12 may be controlled by an X-ray controller 30 disposed within the system controller 24.

Particularly, the X-ray controller 30 is configured to provide power and timing signals to the X-ray source 12.

Further, the system controller 24 is also illustrated as including a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 typically is coupled to or incorporates the system controller 24. The data collected by the data acquisition system 34 may be transmitted to the computer 36 for subsequent processing and reconstruction. The computer 36 may include or communicate with a memory 38 that can store data processed by the computer 36 or data to be processed by the computer 36. It should be understood that any type of memory configured to store a large amount of data might be utilized by such an exemplary system 10. Moreover, the memory 38 may be located at the acquisition system or may include remote components, such as network accessible memory media, for storing data, processing parameters, and/or routines for implementing the techniques described below.

The computer 36 may also be adapted to control features such as scanning operations and data acquisition that may be enabled by the system controller 24. Furthermore, the computer 36 may be configured to receive commands and scanning parameters from an operator via an operator workstation 40, which is typically equipped with a keyboard and other input devices (not shown). An operator may thereby control the system 10 via the input devices. Thus, the operator may observe the reconstructed image and other data relevant to the system from computer 36, initiate imaging, and so forth.

A display 42 coupled to the operator workstation 40 may be utilized to observe the reconstructed images. Additionally, the scanned image may also be printed by a printer 44, which may be coupled to the operator workstation 40. The display 42 and printer 44 may also be connected to the computer 36, either directly or via the operator workstation 40. The operator workstation 40 may also be coupled to a picture archiving and communications system (PACS) 46. It should be noted that PACS 46 might be coupled to a remote system 48, such as radiology department information system (RIS), hospital information system (HIS) or to an internal or external network, so that others at different locations may gain access to the projection data.

It should be further noted that the computer 36 and operator workstation 40 may be coupled to other output devices, which may include standard or special purpose computer monitors and associated processing circuitry. One or more operator work stations 40 may be further linked in the system for outputting system parameters, requesting examinations, viewing images, and so forth. In general, displays, printers, work stations, and similar devices supplied within the system may be local to the data acquisition components, or may be remote from these components, such as elsewhere within an institution or hospital, or in an entirely different location, linked to the image acquisition system via one or more configurable networks, such as the Internet, a virtual private network or the like.

Figure 2:
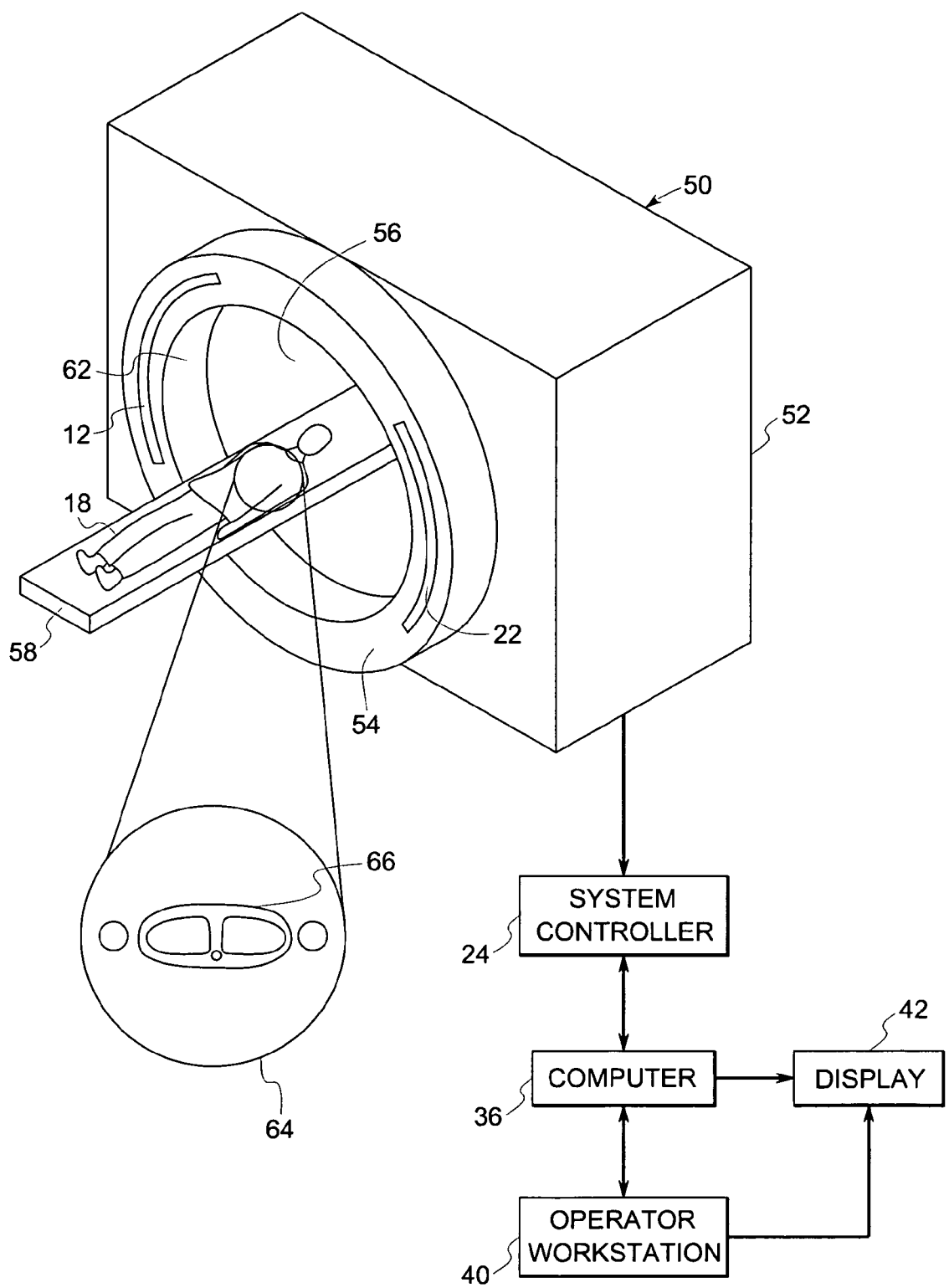
FIG. 2 is a block diagram of a physical implementation of the CT system of FIG. 1.

As noted above, an exemplary imaging system utilized in a present embodiment may be a CT scanning system 50, as depicted in greater detail in FIG. 2. The CT scanning system 50 may be a multi-slice CT (MSCT) system that offers a wide array of axial coverage, high rotational speed of the gantry, and high spatial resolution. Alternately, the CT scanning system 50 may be a volumetric CT (VCT) system utilizing a cone-beam geometry and an area detector to allow the imaging of a volume, such as an entire internal organ of a subject, at high or low gantry rotational speeds. The CT scanning system 50 is illustrated with a frame 52 and a gantry 54 that has an aperture 56 through which a patient 18 may be moved. A patient table 58 may be positioned in the aperture 56 of the frame 52 and the gantry 54 to facilitate movement of the patient 18, typically via linear displacement of the table 58 by the linear positioning subsystem 28 (see FIG. 1). The gantry 54 is illustrated with the source of radiation 12, such as an X-ray tube that emits X-ray radiation from a focal point 62.

In typical operation, the X-ray source 12 projects an X-ray beam from the focal point 62 and toward detector array 22. The collimator 14 (see FIG. 1), such as lead or tungsten shutters, typically defines the size and shape of the X-ray beam that emerges from the X-ray source 12. The detector 22 is generally formed by a plurality of detector elements, which detect the X-rays that pass through and around a subject of interest, such as the heart or chest. Each detector element produces an electrical signal that represents the intensity of the X-ray beam at the position of the element during the time the beam strikes the detector. The gantry 54 is rotated around the subject of interest so that a plurality of radiographic views may be collected by the computer 36.

Thus, as the X-ray source 12 and the detector 22 rotate, the detector 22 collects data related to the attenuated X-ray beams. Data collected from the detector 22 then undergoes pre-processing and calibration to condition the data to represent the line integrals of the attenuation coefficients of the scanned objects. The processed data, commonly called projections, may then be filtered and back projected to formulate an image of the scanned area. A formulated image may incorporate, in certain modes, projection data for less or more than 360 degrees of rotation of the gantry 54.

Once reconstructed, the image produced by the system of FIGS. 1 and 2 reveals internal features 66 of the patient 18. In traditional approaches for the diagnosis of disease states, and more generally of medical conditions or events, a radiologist or physician would consider the reconstructed image 64 to discern characteristic features of interest. In cardiac imaging, for example, such features 66 include coronary arteries or stenotic lesions of interest, and other features, which would be discernable in the image, based upon the skill and knowledge of the individual practitioner. Other analyses may be based upon capabilities of various algorithms, such as algorithms generally referred to as computer aided detection or computer aided diagnosis (CAD) algorithms.

As noted previously, the present technique is directed to combining data from a generally standard pixel and a sub-pixel weighted inversely by the associated noise. Further, a correction algorithm that combines the pixel pile-up correction with the data from both the standard pixel and the sub-pixel is presented. It should be noted that each detector element of a detector is commonly referred to as a "pixel". In a conventional sense, then, the pixel generally represents the smallest area unit that can be resolved by the detector. In the present context, however, each "pixel" may be further broken down into sub-regions to improve the ability to count X-ray or high energy photons and thereby improve performance of the detector and avoid the effects of pile-up.

Figure 3:
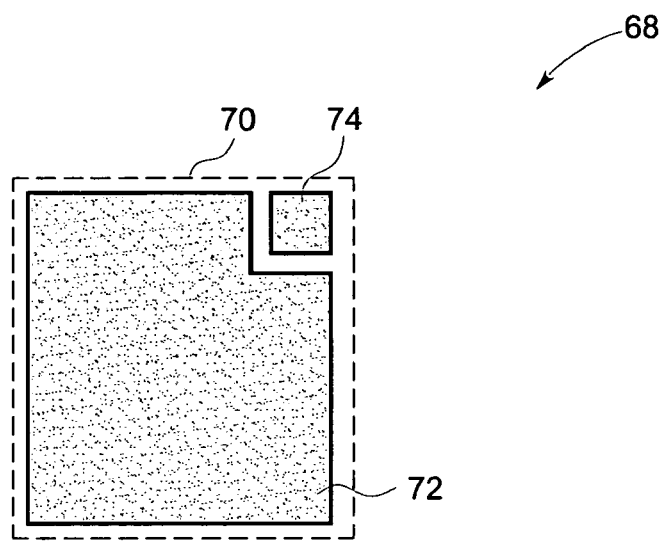
FIG. 3 is a top view of an exemplary detector element area illustrating asymmetrical sub-pixelization, in accordance with aspects of the present technique.

Referring now to FIG. 3, a top view 68 of an exemplary CT detector element illustrating asymmetrical sub-pixelization is depicted. Reference numeral 70 is representative of a single detector element. It should be noted that the terms detector element and pixel may be used interchangeably. In one embodiment, the pixel 70 may be pixelated into two separate sub-pixels that have different flux rate characteristics, for example. As depicted in FIG. 3, the pixel 70 is shown as having a first region 72 and a second region 74. Moreover, the first region 72 has a first area. Also, the second region 74 has a second area. Additionally, as depicted in FIG. 3, the first area associated with the first region 72 of the pixel 70 is substantially larger than the second area associated with the second region 74 of the pixel 70. Consequently, the asymmetry in the areas associated with the sub-pixels 72, 74 results in a composite pixel area with different saturation thresholds within the composite pixel area.

In the illustrated embodiment, an asymmetry ratio AR associated with the first and second regions 72, 74 may be defined as:

$$AR = \frac{\text{area of first region}}{\text{area of second region}}. \quad (1)$$

For example, in one embodiment, the asymmetry ratio AR may be 10:1. Accordingly, the first region 72 of the pixel 70 may be 10× larger than the second region 74. Consequently, with all conditions being the same, it is likely that the second region 74 will saturate at an X-ray flux threshold 10× that of the first region 72. It should be noted that although the exemplary embodiments illustrated hereinafter are described in the context of the sub-pixelation illustrated in FIG. 3, any number of orientations of the first region 72 relative to the second region 74 are contemplated in conjunction with the present technique. In other words, asymmetry ratios AR of 5:1, 20:1 and others are also contemplated, as well as different physical layouts for the two regions or areas.

It should also be noted that each of the first and second regions 72, 74 of the pixel 70 may be configured to saturate at a predetermined count rate level. Furthermore, each of the first and second regions 72, 74 of the pixel 70 may also be configured to count photons received and associate an energy level to each photon counted or place photons into one or more energy bins according to their detected energy level.

As will be appreciated, detectors such as direct conversion photon counting detectors, saturate due to the intrinsic charge collection time (i.e., dead time) associated with each X-ray photon event. Consequently, the direct conversion photon counting detectors suffer from drawbacks such as decreased DQE at high count rates due to detector pile-up. In other words, in direct conversion photon counting detectors, there is a dead-time associated with the time required to detect and count an incident photon. If another photon impinges on the detector during this dead-time, the resulting flux rate measured by the detector is not a true representation of the incident flux rate. As a result a relationship between the incident flux rate ($R_{in}$) and the measured flux rate ($R_{out}$) becomes non-linear, dropping off as the count rate is increased. This drop off is represented by the decrease in the relative DQE due to pile up which is equal to the ratio $R_{out}/R_{in}$. Furthermore, saturation occurs due to pulse pile-up when the X-ray photon absorption rate for each pixel is on the order of the inverse of this charge collection time.

Figure 4:
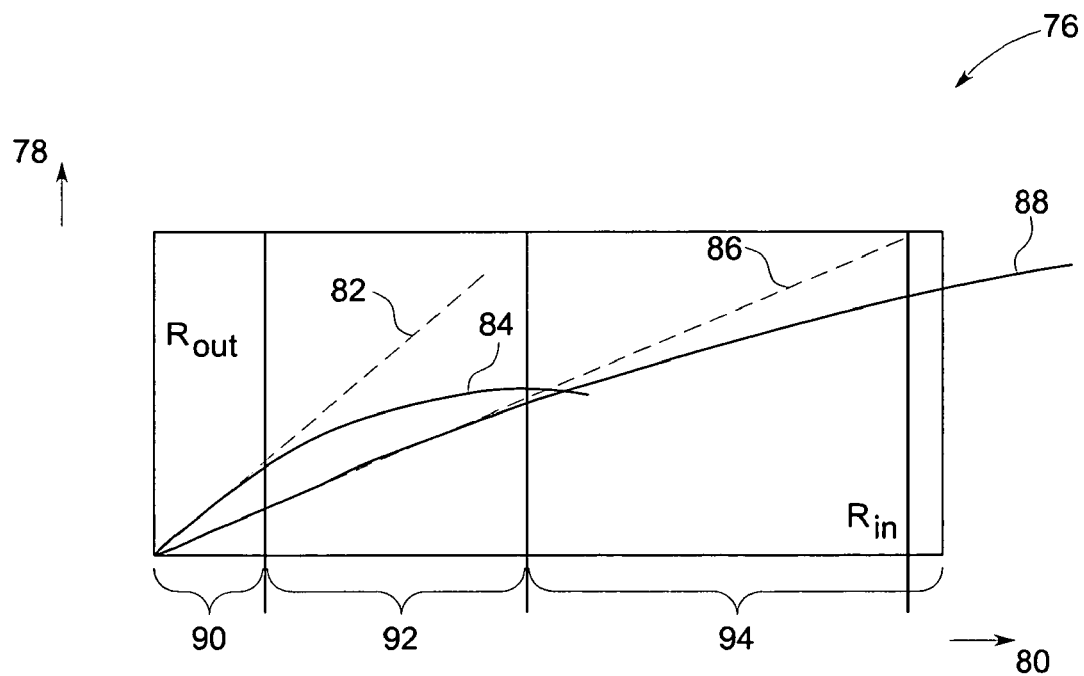
FIG. 4 is an illustration of pile-up correction, in accordance with aspects of the present technique.

Accordingly, a method for correcting pile-up defects is presented. FIG. 4 is an illustration of pile-up correction 76, in accordance with aspects of the present technique. As depicted in FIG. 4, a variation in counts per second 78 is plotted against a variation in incident flux rate 80. As will be appreciated, the flux rate embodies the number of photons detected by a pixel with an associated area per unit time. Reference numeral 82 indicates a desirable response curve representative of the variation of counts per second as a function of the incident flux associated with the first region 72 of the pixel 70. Further, reference numeral 84 is representative of number of photons per second counted by the first region 72 (see FIG. 3). In other words, the response curve 84 embodies the count rate measured by the first region 72. In a similar fashion, reference numeral 86 indicates a desirable response curve representative of the variation of counts per second as a function of the incident flux associated with the second region 74 of the pixel 70. Moreover, reference numeral 88 is representative of number of photons counted by the second region 74 (see FIG. 3). Also, reference numerals 90, 92 and 94 are representative of a first section, a second section, and a third section of the graphical illustration 76 and will be described in greater detail hereinafter.

As depicted in FIG. 4, the relationship between the desirable response curve 82 and the measured response curve 84 associated with the first region 72 of the pixel 70 is most linear in the first section 90. However, as depicted in FIG. 4, the relationship between the desirable response curve 82 and the measured response curve 84 tends to become non-linear in the second section 92 and drops off as the count rate is increased. In a similar fashion, the relationship between the desirable response curve 86 and the measured response curve 88 representative of the flux measured by the second region 74 of the pixel 70 is most linear in the first and second sections 90, 92, but tends to become non-linear in the third section 94 as the count rate is increased. The actual number of photons counted in regions 72 and 74 depicted by response curves 84 and 86, respectively, are lower than the desirable response curve due to the pulse pile-up effect. The difference in the slope of the desirable response curves 82 and 86 is due to the difference in the area of the corresponding pixels 72 and 74, and the difference may be described by the asymmetry ratio AR (see equation 1).

Figure 5:
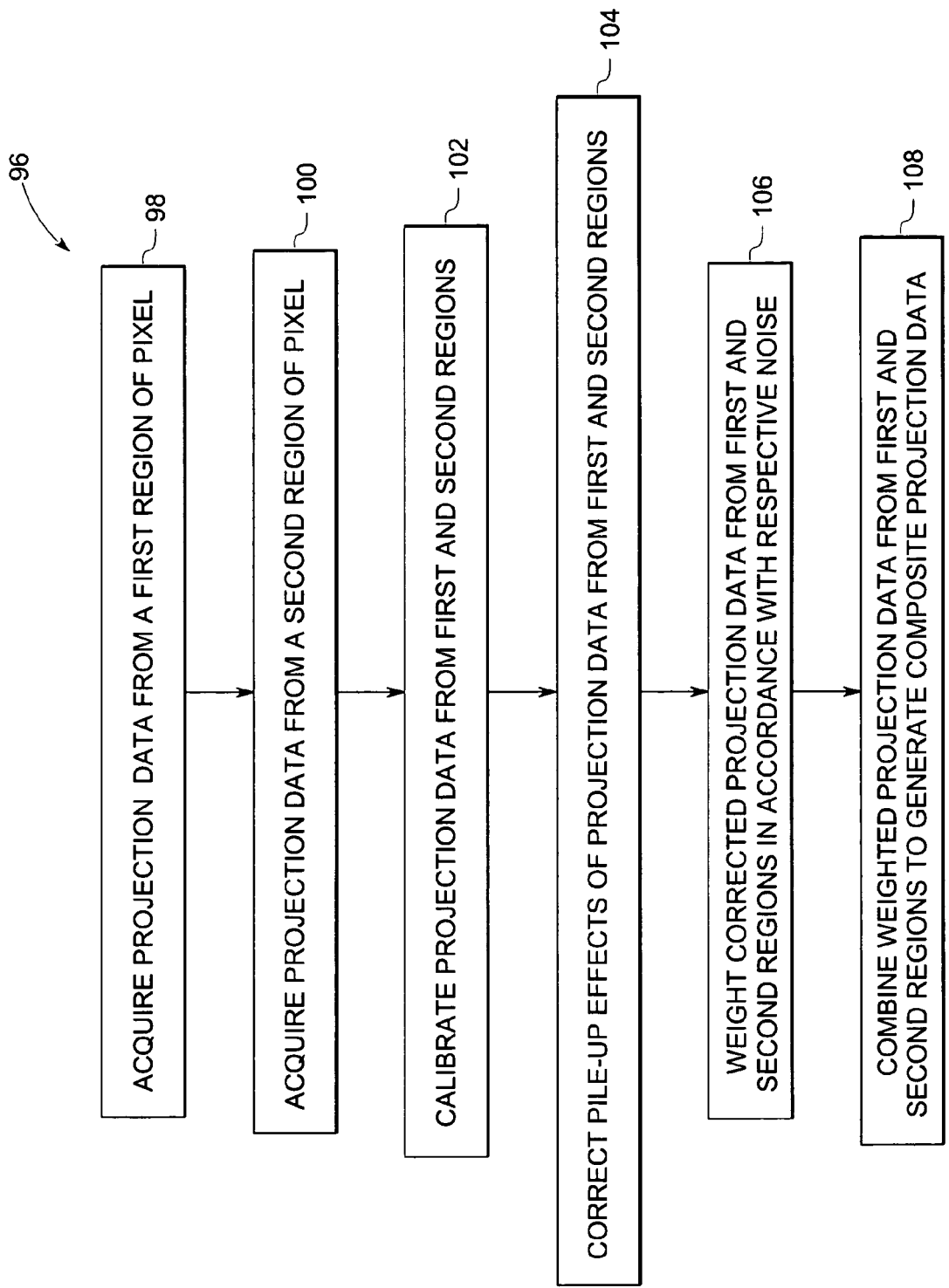
FIG. 5 is a flow chart illustrating an exemplary process of over-ranging and pile-up correction, in accordance with aspects of the present technique.

FIG. 5 is a flow chart of exemplary logic 96 for scanning a volume to be imaged. In accordance with exemplary aspects of the present technique, the method includes optimally combining information from the first and second regions 72, 74 (see FIG. 3) of the pixel 70 (see FIG. 3) taking into account associated noise thereby extending flux rate capability of the pixel 70.

The method starts at step 98 where projection data from a first region, such as the first region 72 (see FIG. 3) of a pixel, such as the pixel 70 (see FIG. 3) is acquired. As previously noted with reference to FIG. 3, the first region may have a first area. Subsequently, at step 100, projection data from a second region, such as the second region 74 (see FIG. 3) may be acquired. The second region 74 may have a second area, as previously noted. Typically, the data from the first and second regions is acquired over the same time period.

Following step 100, the projection data acquired from the first and second regions of the pixel may be calibrated at step 102 to accommodate the difference in effective collection area. In one embodiment, two calibration factors may be required to convert the measured count rate to incident flux rate for each of the first and second regions 72 and 74.

In one embodiment of step 102, the projection data (i.e., measured count rate) acquired from each of the first and second regions may be calibrated by measuring under conditions of uniform illumination the count rate as a function of the input X-ray flux and fitting that function to a polynomial function by extrapolating from a lower part of the curve. This procedure is illustrated in FIG. 4 where the count rate response 84 of the first region 72 and the count rate response 88 of the second region 74 are fitted to the respective linear response curves 82 and 86 which are representative of an extrapolation of a low count rate behavior. In one embodiment, the low count rate may be considered to be less than 1/20 the maximum periodic rate. Further, the inverse of the slope of the response curves 84 and 88 may then be employed as calibration factors in step 102, where the calibration factors are utilized to convert the measured count rate to the incident flux rate. The smaller area of second region 74 leads to a smaller slope of desired response 86 and a larger calibration factor for the projection data acquired from the second region 74. The projection data is then multiplied by the calibration factor to convert the measured count rate to incident flux rate.

As previously noted, the response curves 84, 88 representative of the count rate measured by the first and second regions tend to become non-linear as the flux rate is increased. Therefore, it is desirable to "correct" the non-linear responses. In one embodiment, the non-linear responses may be corrected by fitting the curve of actual flux versus measured count rate to a polynomial function as will be described hereinafter.

With continuing reference to FIG. 5, in accordance with aspects of the present technique, the fitting step may include correcting pile-up effects in the projection data acquired from each of the first and second regions 72, 74 of the pixel 70. Accordingly, at step 104, the acquired projection data may be corrected for pile-up effects by applying a polynomial fit to the projection data acquired from each of the first and second regions of the pixel. In one embodiment, a third order polynomial may be a functional form of the fit. However, in certain other embodiments, a fourth order polynomial may be employed as a functional form of the fit. Consequent to the application of this polynomial fit, the projection data acquired from each of the first and second regions 72, 74 of the pixel 70 may be corrected for pile-up effects.

It should be noted that steps 102 and 104 maybe effectively combined if the calibration factor is incorporated as a coefficient of a linear term of the polynomial. Furthermore, consequent to the calibration and correction steps 102, 104, the effective count rate capability of the second region 74 of the pixel 70 is enhanced albeit with a penalty of increased noise levels relative to an ideal detector. Also, if the count rate of the second region 74 of the pixel 70 is increased to a point where the relationship between the incident count rate and the incident flux becomes non-monotonic, then this correction may no longer be practical. In this situation, the detector is over-ranged and a current count rate reaches a maximum achievable count rate. Furthermore, as the pile-up effect becomes larger, the loss of DQE is also larger. Therefore, the detector may be designed to cut off at a lower count rate to preserve high count DQE.

Additionally, projection data acquired from the first region 72 of the pixel 70 may be combined with the projection data acquired from the neighboring, smaller-sized second region 74 such that the deleterious DQE effects are reduced. Accordingly, an exemplary method of combining data from the first and second regions 72, 74 of a pixel 70 is presented.

At step 106, the corrected projection data from each of the first and second regions of the pixel may be weighted by an associated uncertainty factor and summed. The uncertainty associated with the projection data acquired from the first and second regions is a function of the number of detected photons and the DQE of the detector. In one embodiment, the uncertainty may include noise associated with projection data acquired from each of the first and second regions of the pixel. Accordingly, projection data acquired from each of the first and second regions may be weighted employing the graph 76 illustrated in FIG. 4. As previously noted, reference numerals 90, 92, and 94 are representative of a first section, a second section and a third section respectively of the graph 76. The first section 90 is representative of a region of the graph 76 where the projection data acquired via the first region 72 of the pixel 70 is weighted the most. In addition, the second section of the graph 76 embodies a region of the graph where the projection data acquired from the first region 72 of the pixel 70 is corrected for pile-up effects and the projection data acquired via the second region 74 of the pixel 70 may be employed to constrain the correction factor. For example, in the case where the measured response curve 84 is non-monotonic and has two incident flux rates corresponding to one measured count rate, the value of the response curve 88 will decide the appropriate incident flux rate. Moreover, the third section 94 of the graph 76 is representative of a region of the graph 76 where the projection data acquired by the second region 74 of the pixel 70 is weighted the most and the projection data may also be corrected for pile-up effects.

Following the weighting step 106, weighted projection data associated with each of the first and second regions of the pixel may then be combined to generate composite projection data at step 108. Assuming Poisson's statistics, the variance of the projection data acquired by the first and second regions may be computed as:

$$\sigma_A^2 = N_A \text{DQE}(N_A)$$

and $$\sigma_B^2 = N_B \text{DQE}(N_B). \tag{2}$$

In equation (2), $\sigma_A^2$ and $\sigma_B^2$ embody the variance associated with the projection data acquired from the first and second regions 72, 74 respectively. Also, $\sigma_A^2$ and $\sigma_B^2$ may be computed by the product of projection data from each of the first and second regions weighted by their noise as depicted by equation (2). In one embodiment, the variances $\sigma_A^2$ and $\sigma_B^2$ associated with projection data acquired from the first and second regions may be representative of a measure of uncertainty associated with each of the respective sets of projection data. Also, in equation (2), $N_A$ and $N_B$ are representative of the number of X-ray photons counted by the first and second regions 72, 74 of the pixel 70 respectively. Further, as will be appreciated, DQE is indicative of detector quantum efficiency of the pixel 70 and is a measurable quantity. Additionally, $\text{DQE}(N_A)$ and $\text{DQE}(N_B)$ are the DQE values associated with the number of photons counted $N_A$, $N_B$ by the first and second regions respectively. In accordance with aspects of the present technique, DQE $(N_A)$ and $\text{DQE}(N_B)$ values may be obtained via a look-up table. For example, a look-up table 110 illustrated in FIG. 6 may be employed to obtain the values of $\text{DQE}(N_A)$ and $\text{DQE}(N_B)$.

Subsequently, a composite signal C may be computed by the sum of the signals from the first and second regions weighted by their associated noise as follows:

$$C = \left(\frac{1}{\sigma_A^2} + \frac{1}{\sigma_B^2}\right)^{-1}\left(\frac{A}{\sigma_A^2} + \frac{B}{\sigma_B^2}\right) \quad (3)$$

In equation (3), A and B are representative of projection data acquired from the first and second regions respectively. It may be shown that the uncertainty associated with the composite signal C that has been combined based on equation (3) is less than or equal to the uncertainty associated with combining the two measurements without weighting and is in fact a minimum projection data. Further, as may be observed from equation (3), if the uncertainty $\sigma_A^2$ or $\sigma_B^2$ of one signal A or B, respectively, is large, then it makes less contribution to the composite signal C.

Additionally, the correction algorithm may also be applied to correct over-ranging effects. If the first region 72 of the pixel 70 over-ranges, then the projection data associated with the pixel 70 may be replaced by the calibrated and pile-up corrected projection data from the second region 74. Consequently, at high count rates above which the first region 72 of the pixel 70 is saturated, only the projection data from the second region 74 of the pixel 70 used. Alternatively, at low count rates, composite projection data C representative of a weighted sum of the response from both the first and second regions 72, 74 is assigned to the projection for the pixel 70.

It should be noted that parameters associated with the subject being imaged may be acquired. The parameters may include a shape and a size of the subject being imaged, for example. Additionally, the parameters may also include a diagnostic exam type and a visualization mode. An image may then be reconstructed based on the acquired parameters and the composite projection data C.

Figure 6:
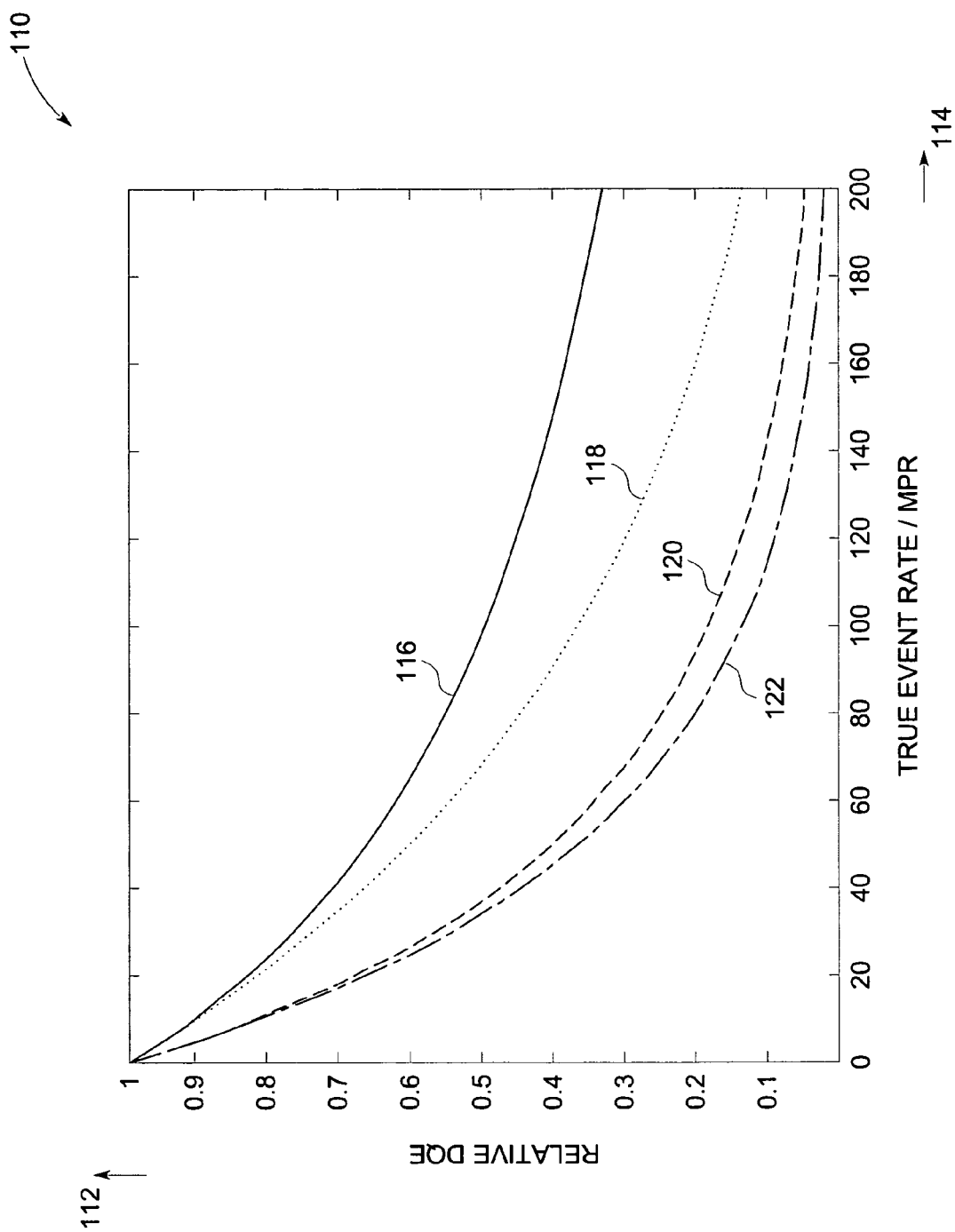
FIG. 6 is a graphical representation of variation of DQE due to pile-up with respect to true event rate/maximum periodic rate.

FIG. 6 is a graphical representation 110 of variation of a relative DQE 112 with a variation in true event rate/maximum periodic rate (MPR) 114. A first curve 116 is representative of the variation of the relative DQE 112 with the variation in the true event rate/MPR 114 associated with a non-paralyzable system without pile-up rejection. Additionally, a second curve 118 embodies the variation of the relative DQE 112 with the variation in the true event rate/MPR 114 associated with a paralyzable system without pile-up rejection. Similarly, a third curve 120 corresponds to the variation of the relative DQE 112 with the variation in the true event rate/MPR 114 associated with a non-paralyzable system with pile-up rejection. Also, a fourth curve 122 is representative of the variation of the relative DQE 112 with the variation in the true event rate/MPR associated with a paralyzable system with pile-up rejection. One of the curves 116, 118, 120 and 122 may be matched to the particular characteristics of the detector being used in the system. Such curves measure a ratio between the non-linear measured response curves, such as response curves 84, 88 (see FIG. 4), and the desirable linear response curves such as 82, 86 (see FIG. 4).

The various methods for scanning an object to be imaged and systems for scanning the object to be imaged described hereinabove facilitate use of the techniques presented in a wider variety of CT applications including medical and industrial applications. Furthermore, combining signals from the first and second neighboring regions of the pixel by weighting their value by respective associated noise advantageously reduces the level of noise in the composite signal. Consequently, enhanced contrast detectability in a reconstructed image may be achieved. Additionally, the techniques described hereinabove allow improved use of information from each of the sub-pixels in a direct conversion photon counting detector to achieve enhanced effective count rate. Moreover, the techniques described hereinabove provide an algorithm to combine data from the first and second regions of the pixel weighted inversely by noise associated with a respective region of the pixel 70. Further, a correction algorithm that combines the pixel pile-up correction with the data from both the first and second regions results in enhanced photon counting. Also it is understood that a pixel may be subdivided into more than two regions and image values of the regions may be calibrated, corrected and combined by weighting inverse to the noise to represent the image values for the pixel.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of scanning a subject to be imaged, the method comprising:
   acquiring projection data from a first region of a pixel, wherein the first region has a first area;
   acquiring projection data from a second region of the pixel, wherein the second region has a second area;
   calibrating a measured X-ray flux rate as a function of an incident flux rate for each of the first and second regions;
   correcting the projection data for the first and second regions of the pixel based upon the calibration;
   combining the corrected projection data from the first and second regions to obtain composite projection data for the pixel; and
   storing the composite projection data in a memory.

2. The method of claim 1, wherein the second area is less than the first area.

3. The method of claim 1, wherein each of the first and second regions is configured to count photons received and associate an energy level to each photon counted.

4. The method of claim 1, wherein each of the first and second regions is configured to saturate at a predetermined level.

5. The method of claim 1, wherein calibrating the projection data comprises:
   measuring count rate as a function of input X-ray flux rate; and
   fitting the count rate to a polynomial function.

6. The method of claim 5, wherein the step of fitting comprises correcting pile-up effects in the projection data acquired from each of the first and second regions.

7. The method of claim 1, wherein the step of combining comprises combining the projection data from the first and second regions weighted by associated noise.

8. The method of claim 1, further comprising acquiring parameters associated with the subject to be imaged.

9. The method of claim 8, further comprising reconstructing an image based on the composite projection data and the acquired parameters.

10. A radiographic imaging system comprising a detector assembly configured to detect a stream of radiation emitted by a radiation source toward a subject to be scanned and to generate one or more signals responsive to the stream of radiation, wherein the detector assembly comprises one or more pixels configured to absorb radiation, wherein each of the one or more pixels comprises a first region having a first area and a second region having a second area; and wherein the first area is different from the second area, and wherein the system is configured to measure count rate as a function of input X-ray flux rate, and fit the detected charge to a polynomial function.

11. The system of claim 10, wherein each of the first and second regions is configured to acquire projection data.

12. The system of claim 10, wherein the system is configured to combine the projection data from the first and second regions weighted by associated noise to generate composite projection data.

13. The system of claim 10, wherein the system is configured to acquire parameters associated with the subject.

14. The system of claim 13, wherein the system is configured to reconstruct an image based on the composite projection data and the acquired parameters.

15. The system of claim 10, further comprising a system controller configured to rotate the radiation source and the detector assembly and to acquire one or more sets of projection data from the one or more detectors via a data acquisition system.

16. The system of claim 10, further comprising a computer system operationally coupled to the radiation source and the detector assembly, wherein the computer system is configured to receive the one or more sets of projection data.

17. A computer readable medium comprising one or more tangible media, wherein the one or more tangible media comprise:
    code adapted to acquire projection data from a first region of a pixel, wherein the first region has a first area;
    code adapted to acquire projection data from a second region of the pixel, wherein the second region has a second area;
    code adapted to calibrate a measured X-ray flux rate as a function of an incident flux rate for each of the first and second regions;
    code adapted to correct the projection data for the first and second regions of the pixel based upon the calibration; and
    code adapted to combine the corected projection data from the first and second regions to obtain composite projection data for the pixel.

18. The computer readable medium, as recited in claim 17 further comprising code adapted to calibrate the projection data from each of the first and second regions.

19. The computer readable medium of claim 17, wherein the code adapted to fit comprises code adapted to correct pile-up effects in the projection data acquired from each of the first and second regions.

20. The computer readable medium of claim 17, wherein the code adapted to combine comprises code adapted to combine the projection data from the first and second regions weighted by associated noise.

21. The computer readable medium of claim 17, further comprising code adapted to acquire parameters associated with a subject.

22. The computer readable medium of claim 21, further comprising code adapted to reconstruct an image based on the composite projection data and the acquired parameters.

23. A radiographic imaging system comprising:
    a radiation source configured to emit a stream of radiation toward a subject to be scanned;
    a detector assembly configured to detect the stream of radiation and to generate one or more signals responsive to the stream of radiation wherein the detector assembly comprises one or more pixels configured to absorb radiation, and wherein each of the one or more pixels comprises a first region having a first area and a second region having a second area, wherein the detector assembly is configured to calibrate a measured X-ray flux rate as a function of an incident flux rate for each of the first and second regions, correct the projection data for the first and second regions of the pixel based upon the calibration, and combine the corrected projection data from the first and second regions to obtain composite projection data for the pixel;
    a system controller configured to rotate the radiation source and the detector assembly and to acquire one or more sets of projection data from the one or more detectors via a data acquisition system; and
    a computer system operationally coupled to the radiation source and the detector assembly, wherein the computer system is configured to receive the one or more sets of projection data.

* * * * *